US010001568B2

(12) United States Patent
Teshigawara (10) Patent No.: US 10,001,568 B2
(45) Date of Patent: Jun. 19, 2018

(54) X-RAY COMPUTED TOMOGRAPHY APPARATUS, MEDICAL IMAGE PROCESSING APPARATUS AND MEDICAL IMAGE PROCESSING METHOD (71) Applicant: TOSHIBA MEDICAL SYSTEMS CORPORATION, Otawara-Shi (JP)

(72) Inventor: Manabu Teshigawara, Otawara (JP)

(73) Assignee: Toshiba Medical Systems Corporation, Otawara-Shi (JP)

(*) Notice: Subject to any disclaimer, the term of this patent is extended or adjusted under 35 U.S.C. 154(b) by 375 days.

(21) Appl. No.: 14/753,608

(22) Filed: Jun. 29, 2015

(65) Prior Publication Data
US 2015/0297162 A1 Oct. 22, 2015

Related U.S. Application Data (63) Continuation of application No. PCT/JP2014/050258, filed on Jan. 9, 2014.

(30) Foreign Application Priority Data

Jan. 10, 2013 (JP) .................................. 2013-002894
Jan. 9, 2014 (JP) .................................. 2014-002390

(51) Int. Cl.
*A61B 6/06* (2006.01)
*G01T 1/29* (2006.01)
(Continued)

(52) U.S. Cl.
CPC .......... *G01T 1/2928* (2013.01); *A61B 6/4266* (2013.01); *G01N 23/20091* (2013.01);
(Continued)

(58) Field of Classification Search
CPC .... A61B 6/00; A61B 6/03; A61B 6/06; A61B 6/42; A61B 6/4208; A61B 6/4233;
(Continued)

(56) References Cited

U.S. PATENT DOCUMENTS 5,293,195 A 3/1994 Berlad et al.
5,434,414 A 7/1995 Berlad et al.
(Continued)

FOREIGN PATENT DOCUMENTS

CN 104023639 A 9/2014
JP 61-240146 A 10/1986
(Continued)

OTHER PUBLICATIONS

Combined Chinese Office Action and Search Report dated Feb. 27, 2017 in Chinese Patent Application No. 201480004222.9 (with English translation of categories of cited documents).
(Continued)

*Primary Examiner* — Anastasia Midkiff
(74) *Attorney, Agent, or Firm* — Oblon, McClelland, Maier & Neustadt, L.L.P.

(57) ABSTRACT

According to one embodiment, an X-ray computed tomography apparatus includes an X-ray tube, collimators including through holes respectively collimating an X-ray and diffraction bodies provided in the holes respectively, diffracting the X-ray at an angle to an X-ray energy, X-ray detection elements provided at predetermined distances from the bodies, counting circuitry counting the number of photons originating from the X-ray, storage circuitry storing statistical information, corresponding to energy bins in the X-ray, concerning a count distribution of count values with positions of the elements, classification circuitry classifying the numbers of counted photons for the bins by using the information, reconstruction circuitry reconstructing a medical image to the bins based on the number of photons classified for the bins.

18 Claims, 9 Drawing Sheets (51) Int. Cl.

| | |
|---|---|
| *G01N 23/20* | (2018.01) |
| *G21K 1/02* | (2006.01) |
| *G21K 1/06* | (2006.01) |
| *G02B 5/02* | (2006.01) |
| *G02B 27/42* | (2006.01) |
| *G01T 1/24* | (2006.01) |
| *G02B 27/09* | (2006.01) |
| *G02B 5/18* | (2006.01) |
| *A61B 6/03* | (2006.01) |
| *A61B 6/00* | (2006.01) |

(52) U.S. Cl.
CPC ............ *G01T 1/247* (2013.01); *G01T 1/2914* (2013.01); *G02B 5/0278* (2013.01); *G02B 27/0944* (2013.01); *G21K 1/02* (2013.01); *G21K 1/06* (2013.01); *A61B 6/032* (2013.01); *A61B 6/06* (2013.01); *A61B 6/4035* (2013.01); *A61B 6/482* (2013.01); *G01N 2223/0563* (2013.01); *G01N 2223/423* (2013.01); *G01T 1/29* (2013.01); *G02B 5/1838* (2013.01); *G02B 27/42* (2013.01)

(58) Field of Classification Search
CPC ....... A61B 6/4266; A61B 6/4291; A61B 6/48; A61B 6/483; A61B 6/485; A61B 2560/00; A61B 2560/04; A61B 2560/06; H01L 27/00; H01L 27/14; H01L 27/142144; H01L 27/1446; H01L 27/146; H01L 27/14601; H01L 27/14609; H01L 27/14618; H01L 27/14625; H01L 27/14641; H01L 27/14643; H01L 27/14658; H01L 27/14659; H01L 27/14663; H01L 27/14665; H01L 27/14676; H01L 27/148; H01L 27/14806; H01L 27/14812; H01L 27/14818; H01L 27/14831; H01L 27/1485; H01L 27/14893; G01T 1/00; G01T 1/15; G01T 1/16; G01T 1/161; G01T 1/18; G01T 1/20; G01T 1/2002; G01T 1/2006; G01T 1/2018; G01T 1/24; G01T 1/243; G01T 1/244; G01T 1/247; G01T 1/249; G01T 1/29; G01T 1/36; G01T 1/362; G01T 1/366; G01T 7/00; G01T 1/2914; G01T 1/2928; G01N 23/00; G01N 23/02; G01N 23/04; G01N 23/046; G01N 23/06; G01N 23/08; G01N 23/083; G01N 23/087; G01N 23/20; G01N 23/2008; G01N 23/20091; G01N 2223/00; G01N 2223/03–2223/05; G01N 2223/056; G01N 2223/0563; G01N 2223/30; G01N 2223/316; G01N 2223/40; G01N 2223/413; G01N 2223/419; G01N 2223/423; G01N 2223/50; G01N 2223/501; G01N 2223/505; G01N 2223/5055; G21K 1/00; G21K 1/02; G21K 1/06; G21K 2201/00; G21K 2201/06; G21K 2201/062; G21K 2201/067; G02B 5/00; G02B 5/005; G02B 5/02; G02B 5/0273; G02B 5/0278; G02B 5/18; G02B 5/1838; G02B 5/1842; G02B 5/1866; G02B 6/00; G02B 6/0011; G02B 6/0033; G02B 6/005; G02B 6/0051; G02B 6/0096; G02B 27/0944; G02B 27/1086; G02B 27/30; G02B 27/42; G02B 27/4205; G02B 27/4277; G02B 27/4233; G02B 27/4244; G02B 27/4294; G01R 23/02; G01R 23/10

See application file for complete search history.

(56) References Cited

U.S. PATENT DOCUMENTS

| | | | |
|---|---|---|---|
| 5,438,202 | A | 8/1995 | Matanzon et al. |
| 5,530,248 | A | 6/1996 | Natanzon et al. |
| 9,693,745 | B2* | 7/2017 | Teshigawara ........ A61B 6/4233 |
| 2009/0225945 | A1* | 9/2009 | Smither ............... G01N 23/046 |
| | | | 378/71 |
| 2009/0302232 | A1* | 12/2009 | Grosholz, Jr. ............ G01T 1/17 |
| | | | 250/394 |
| 2010/0020922 | A1 | 1/2010 | Carmi |
| 2010/0187432 | A1 | 7/2010 | Herrmann et al. |
| 2015/0173694 | A1 | 6/2015 | Teshigawara |

FOREIGN PATENT DOCUMENTS

| | | | |
|---|---|---|---|
| JP | 7-5263 | A | 1/1995 |
| JP | 2004-347502 | A | 12/2004 |
| JP | 2010-500119 | A | 1/2010 |
| JP | 2010-530535 | A | 9/2010 |
| JP | 2011-24773 | A | 2/2011 |

OTHER PUBLICATIONS

International Search Report dated Feb. 10, 2014 for PCT/JP2014/050258 filed on Jan. 9, 2014 with English Translation.

Written Opinion dated Feb. 10, 2014 for PCT/JP2014/050258 filed on Jan. 9, 2014.

* cited by examiner

X-RAY COMPUTED TOMOGRAPHY APPARATUS, MEDICAL IMAGE PROCESSING APPARATUS AND MEDICAL IMAGE PROCESSING METHOD

CROSS-REFERENCE TO RELATED APPLICATIONS

This application is a Continuation Application of PCT Application No. PCT/JP2014/050258, filed Jan. 9, 2014 and based upon and claims the benefit of priority from the Japanese Patent Application No. 2013-002894, filed Jan. 10, 2013 and the Japanese Patent Application No. 2014-002390, filed Jan. 9, 2014, the entire contents of all of which are incorporated herein by reference.

FIELD

Embodiments described herein relate generally to an X-ray computed tomography apparatus, a medical image processing apparatus and a medical image processing method.

BACKGROUND

Recently, attempts to commercialize photon counting type X-ray computed tomography apparatuses (to be referred to as photon counting X-ray CT apparatuses hereinafter) have been made in the form of the extension of techniques concerning single photon detection (to be referred to as single photon detection techniques hereinafter) in nuclear medicine diagnosis apparatuses such as single photon emission computed tomography apparatuses (to be referred to as SPECT apparatuses hereinafter) and positron emission computed tomography apparatuses (to be referred to as PET apparatuses hereinafter). The single photon detection techniques are roughly classified into two types.

The first single photon detection technique is the following method. First of all, a crystal (scintillator) or the like converts X-rays transmitted through an object into scintillation light. A photodetector such as a photomultiplier tube (to be referred to as a PMT hereinafter) or a silicon photomultiplier (to be referred to as an SiPM hereinafter) detects the scintillation light to extract X-ray photons as electrical signals. The above method is called an indirect conversion type method.

The second single photon detection technique is a method of directly converting X-ray photons transmitted through an object into electrical signals by using a semiconductor detector (this method is also called a direct conversion type method). More specifically, a bias voltage is applied to the two electrodes of the semiconductor detector in advance. When X-ray photons enter the semiconductor detector, electron/hole pairs are generated inside the semiconductor detector. The generated electrons and holes are attracted to the different electrodes, respectively. The electrons reaching the electrode are extracted as electrical signals.

In either of the above methods, since the integral value of the intensity of each extracted electrical signal (to be referred to as a detection signal hereinafter) is proportional to the energy of X-ray photons, detection signals are integrated. Integrating detection signals will calculate the energy of each detected X-ray photon. A difference between a nuclear medicine diagnosis apparatus and a photon counting X-ray CT apparatus is that the flow rate of photons in the photon counting X-ray CT apparatus is much higher than that in the nuclear medicine diagnosis apparatus. In order to reconstruct a medical image by using the photon counting X-ray CT apparatus, it is necessary to perform single photon detection at a rate of, for example, $10^9$ photons/mm$^2$/sec (to be referred to as a count rate hereinafter).

When, however, executing single photon detection with respect to X-ray photons at the above count rate, problems arise concerning the following two types of count losses respectively corresponding to the above two types of single photon detection techniques. The problem in the first single photon detection technique concerns a count loss caused by pileup. Pileup occurs when a plurality of X-ray photons enter a scintillator within the typical decay time (several ns) of scintillation. Pileup is a phenomenon in which a plurality of detection signals respectively corresponding to a plurality of X-ray photons overlap. When pileup occurs, a plurality of X-ray photons are counted as one X-ray photon, resulting in a count loss.

The problem concerning the second single photon detection technique concerns a count loss caused when X-ray photons enter the semiconductor detector during the dead time of the semiconductor detector. The dead time is the time interval from the instant a detection signal is extracted from the semiconductor detector to the instant the semiconductor detector can perform pair generation again. When X-ray photons enter the semiconductor detector in the dead time, since no pair generation occurs, no X-ray photons are counted. Currently, there have been attempts to decrease the number of X-ray photons entering the same semiconductor detector within a unit time by decreasing the size (pixel size) of the semiconductor detector. In such attempts, however, the maximum count rate remains at about $10^6$ photons/mm$^2$/sec.

A reason for such problems concerning the above count loss is that a detection signal with a long decay time constant is integrated to calculate the energy of an X-ray photon entering the X-ray detector. In order to implement a photon counting X-ray CT apparatus, it is necessary to achieve a high count rate. It is however difficult to find the above single photon detection techniques on the extension of techniques concerning nuclear medicine diagnosis apparatuses.

As a method of solving the above problems, for example, a method using an X-ray diffraction phenomenon is available. In this method, a diffraction body is provided on the rear surface side of a collimator. A plurality of X-ray detection elements are provided at predetermined distances from the diffraction body. A polychromatic X-ray entering a collimator is diffracted (scattered) at diffraction angles corresponding to the energies of a plurality of monochromatic X-rays included in the polychromatic X-ray. This diffraction causes the polychromatic X-ray to be diffracted (scattered) in the form of Debye-Scherrer rings on a plurality of X-ray detection elements. A histogram representing the number of X-ray photons with respect to the radii of Debye-Scherrer rings is the overlap of the photon count of diffracted X-rays and the photon count of non-diffracted X-rays (transmitted X-rays). In addition, if the distances between the diffraction body and a plurality of X-ray detection elements are short, since a plurality of Debye-Scherrer rings respectively corresponding to a plurality of monochromatic X-rays overlap each other, it is difficult to obtain the energy spectrum of a polychromatic X-ray.

DETAILED DESCRIPTION

In general, according to one embodiment, an X-ray computed tomography apparatus includes an X-ray tube, collimators, X-ray detection elements, counting circuitry, storage circuitry, classification circuitry, reconstruction circuitry.

The X-ray tube generates X-rays.

The collimators includes through holes respectively which collimate the X-ray generated by the X-ray tube and diffraction bodies provided in the through holes respectively, diffracting the X-ray at an angle corresponding to an energy of the X-ray.

The X-ray detection elements is provided at predetermined distances from each of the diffraction bodies.

The counting circuitry count the number of photons originating from the X-ray based on outputs from the X-ray detection elements.

The storage circuitry store statistical information, corresponding to energy bins in the X-ray, concerning a count distribution of a plurality of count values with positions of the X-ray detection elements.

The classification circuitry classify the numbers of counted photons for each of the energy bins by using the statistical information.

The reconstruction circuitry reconstruct a medical image corresponding to each of the energy bins based on the number of photons classified for each of the energy bins.

Embodiments of an X-ray computed tomography apparatus based on photon counting (to be referred to as a photon counting X-ray CT apparatus hereinafter) will be described with reference to the accompanying drawings. Note that X-ray computed tomography apparatuses include various types of apparatuses, e.g., a rotate/rotate-type apparatus in which the X-ray generation unit and the X-ray detection unit rotate together around an object, and a stationary/rotate-type apparatus in which many X-ray detection elements arrayed in the form of a ring are fixed, and only the X-ray generation unit rotates around an object. Either type can be applied to this embodiment. In order to reconstruct a medical image, projection data corresponding to one rotation around an object, i.e., 360°, is required, or (180°+fan angle) projection data is required in the half scan method. Either reconstruction scheme can be applied to the embodiment. Recently, with advances toward the commercialization of a so-called multi-tube type X-ray computed tomography apparatus having a plurality of pairs of X-ray generation units and X-ray detection units mounted on a rotating ring, related techniques have been developed. This embodiment can be applied to both a conventional single-tube type X-ray computed tomography apparatus and a multi-tube type X-ray computed tomography apparatus. The single-tube type X-ray computed tomography apparatus will be exemplified here.

Note that the same reference numerals in the following description denote constituent elements having almost the same functions and arrangements, and a repetitive description will be made only when required.

Figure 1:
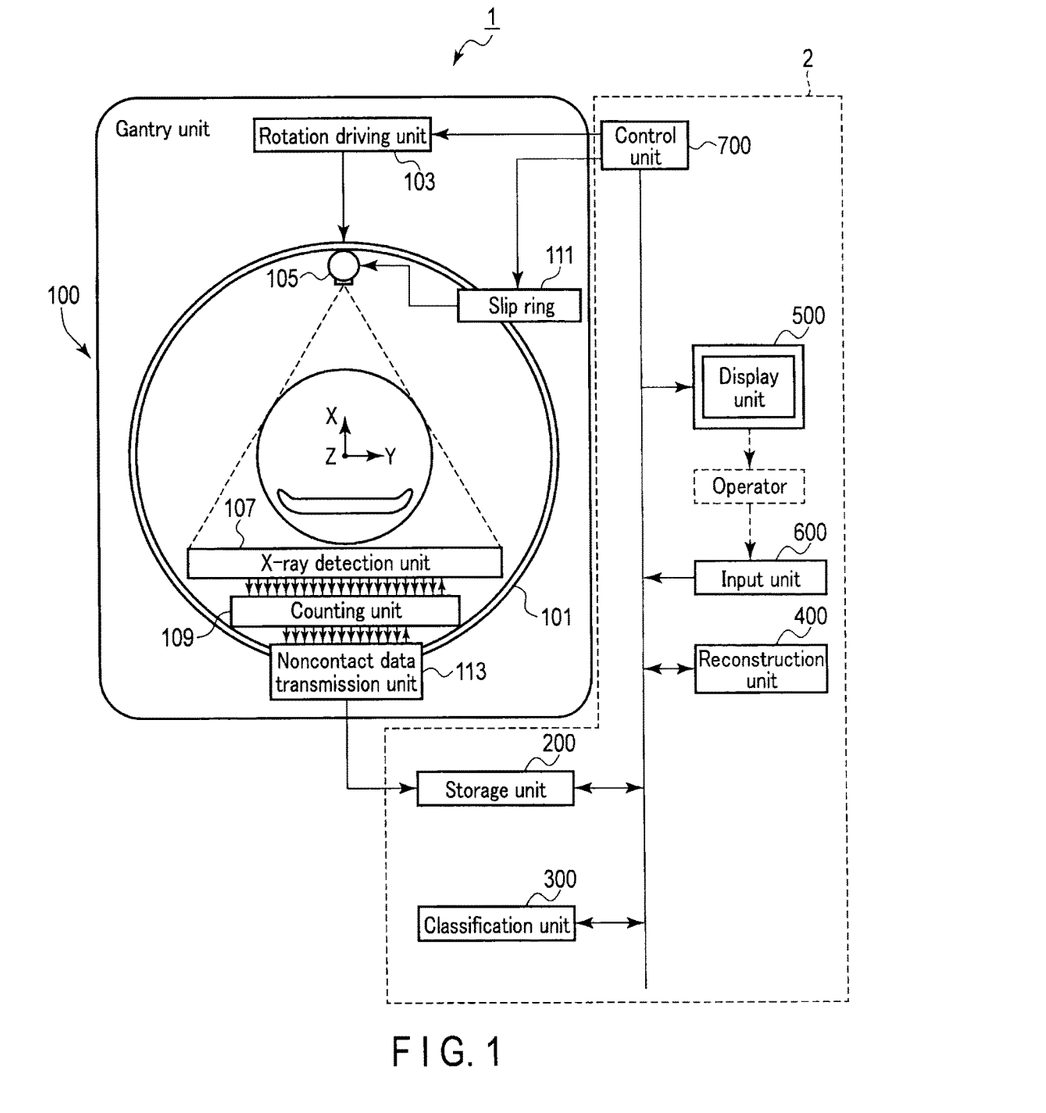
FIG. 1 is a block diagram showing an example of the arrangement of an X-ray computed tomography apparatus according to an embodiment.

FIG. 1 is a block diagram showing an example of the arrangement of a photon counting X-ray CT apparatus according to this embodiment. A photon counting X-ray CT apparatus 1 includes a gantry unit 100, a storage unit 200, a classification unit 300 and a reconstruction unit 400, a display unit 500, an input unit 600, and a control unit 700.

A rotating support mechanism is housed in the gantry unit 100. The rotating support mechanism includes a rotating ring 101, a ring support mechanism supporting the rotating ring 101 so as to allow it to rotate about a rotation axis Z and a rotation driving unit (electric motor) 103 driving the rotation of the rotating ring 101. The rotating ring 101 is equipped with an X-ray generation unit 105, an X-ray detection unit 107, and a counting unit 109 which counts the number of photons originating from X-rays based on outputs from the X-ray detection unit 107.

The X-ray generation unit includes a high voltage generator and an X-ray tube (not shown). The high voltage generator generates a high voltage (to be referred to as a tube voltage hereinafter) to be applied to the X-ray tube and a current (to be referred to as a tube current hereinafter) to be supplied to the X-ray tube. The high voltage generator generates a tube voltage and a tube current in accordance with control signals input from the control unit 700 (to be described later) via a slip ring 111. The X-ray tube emits X-rays from the X-ray focus upon receiving a tube voltage and a tube current from the high voltage generator. The X-ray tube generates polychromatic X-rays. A polychromatic X-ray is constituted by monochromatic X-rays having different energies.

Figure 2:
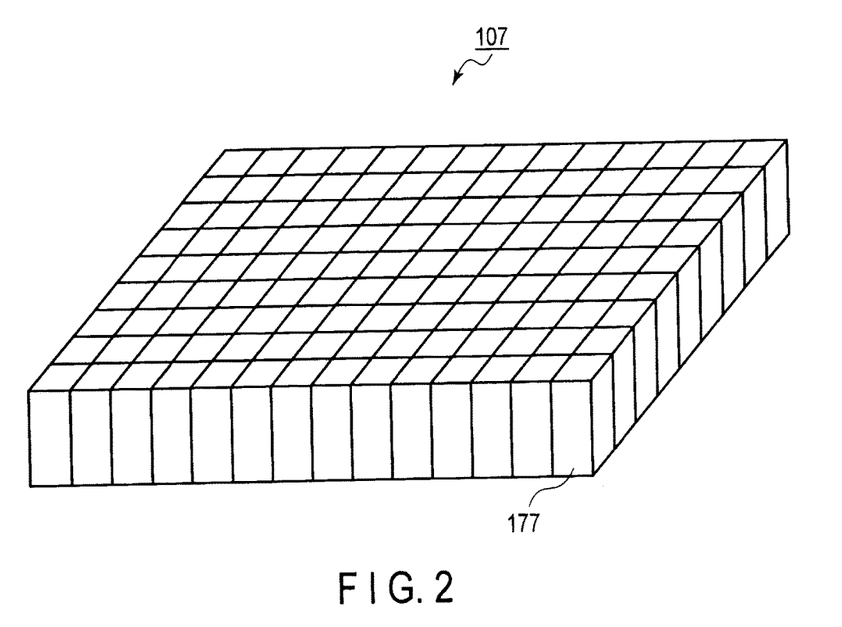
FIG. 2 is a perspective view showing an example of the array of a plurality of X-ray detection modules in an X-ray detection unit according to this embodiment.
Figure 3:
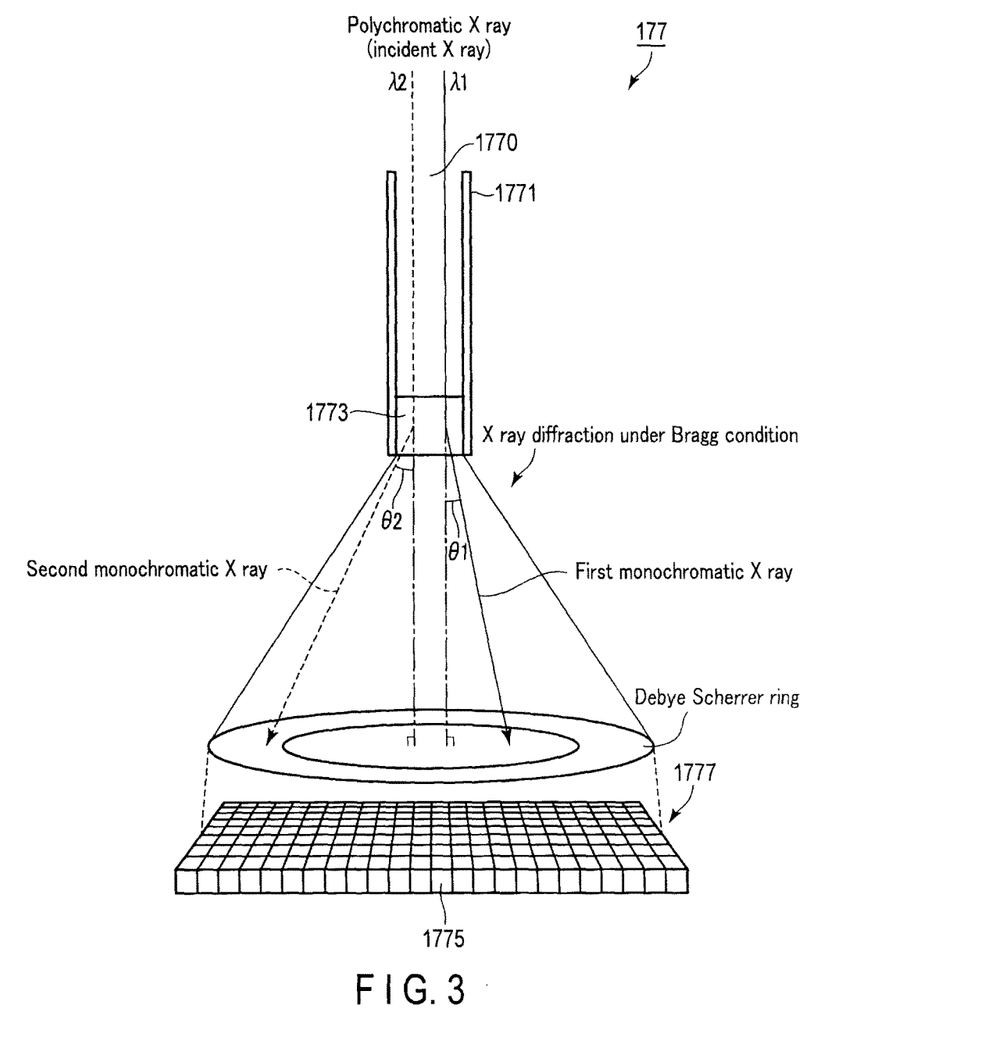
FIG. 3 is a view showing an example of X-ray detection modules in the X-ray detection unit according to this embodiment, together with an incident polychromatic X-ray and X-rays diffracted in accordance with the energies according to the embodiment.

The X-ray detection unit 107 includes a plurality of X-ray detection modules which detect X-rays for the respective energy bins. Assume that in the following description, each of the plurality of X-ray detection modules corresponds to one channel. FIG. 2 is a view showing an example of the array of a plurality of X-ray detection modules 177 in the X-ray detection unit 107. As shown in FIG. 2, the plurality of X-ray detection modules 177 are arrayed in a lattice pattern. Note that, for example, the plurality of X-ray detection modules 177 may be one-dimensionally arrayed along the short axis (Y-axis) direction of the top or the arc direction of the rotating ring 101. FIG. 3 is a view showing an example of the X-ray detection modules 177, together with a polychromatic X-ray (to be referred to as an incident X-ray hereinafter) entering a collimator 1771 and X-rays diffracted by a diffraction body 1773 in accordance with the energies of X-rays.

Each X-ray detection module 177 includes the collimator 1771, the diffraction body 1773, and a plurality of X-ray detection elements 1775. The collimator 1771 has a plurality of through holes 1770. The collimator 1771 collimates incident X-rays through the through holes 1770.

An incident X-ray is a polychromatic X-ray which has received influences such as scattering, absorption, and transmission corresponding to a material on a transmission path in an object and the energies of monochromatic X-rays.

The diffraction body 1773 is provided in the collimator 1771. For example, the diffraction body 1773 is provided on the rear surface side of the collimator 1771. Note that the diffraction body 1773 may be provided on the path of X-rays passing through the through holes 1770. The diffraction body 1773 has a predetermined thickness. The diffraction body 1773 is formed from, for example, a metal or crystal powder. The diffraction body 1773 diffracts a collimated polychromatic X-ray in accordance with the energies. A polychromatic X-ray entering the diffraction body 1773 is a group of polychromatic photons (a group of photons having a plurality of energies respectively corresponding to a plurality of wavelengths). For this reason, the diffraction body 1773 diffracts a group of polychromatic photons at angles corresponding to the energies of the photons under the Black conditions. That is, the diffraction body 1773 diffracts (spectroscopically analyzes) a polychromatic X-ray at angles corresponding to the energies.

The plurality of X-ray detection elements 1775 (to be referred to as an X-ray detection element group 1777 hereinafter) are provided at predetermined distances from the collimator 1771. The X-ray detection element (to be referred to as the central element hereinafter) located in the center of the X-ray detection element group 1777 is provided at a position facing the center of the aperture of the collimator 1771. That is, the collimator 1771 is provided immediately above the central element through the diffraction body 1773. The width of the X-ray detection element group 1777 is larger than the diameter of the collimator 1771. As shown in FIG. 3, the plurality of X-ray detection elements 1775 are two-dimensionally arrayed in a lattice pattern (to be referred to as a two-dimensional array hereinafter). The respective X-ray detection elements 1775 may be one-dimensionally arrayed. Each of the plurality of X-ray detection elements 1775 is connected to a counter 1091 (to be described later). The space between the diffraction body 1773 and the X-ray detection element group 1777 is filled with a material having a small refractive index such as air. Note that the space between the diffraction body 1773 and the X-ray detection element group 1777 may be a vacuum.

More specifically, each of the plurality of X-ray detection elements 1775 is, for example, a pulse generation element. That is, each of the plurality of X-ray detection elements generates a predetermined pulse signal upon reception of an X-ray diffracted by the diffraction body 1773. The X-ray detection element 1775 outputs the generated pulse signal to the counter 1091. The number of pulse signals corresponds to the number of X-ray photons (to be referred to as the photon count hereinafter) originating from a monochromatic X-ray entering the X-ray detection element 1775.

Referring to FIG. 2, assume that a polychromatic X-ray includes a first monochromatic X-ray having a first wavelength $\lambda 1$ and a second monochromatic X-ray having a second wavelength $\lambda 2$. Assume that the first wavelength $\lambda 1$ is shorter than the second wavelength $\lambda 2$. At this time, the Bragg angle of the first monochromatic X-ray is smaller than that of the second monochromatic X-ray. For this reason, a plurality of different monochromatic X-rays included in a polychromatic X-ray entering the diffraction body 1773 are diffracted at different angles corresponding to the energies. If the X-ray detection element group 1777 is a two-dimensional array, a plurality of different monochromatic X-rays arrive on the two-dimensional array in the form of Debye-Scherrer rings corresponding to the energies.

The counting unit (circuitry) 109 counts the pulse signals output from each of the plurality of X-ray detection elements 1775 in each of the plurality of X-ray detection modules 177. That is, the counting unit 109 counts the count of X-ray photons entering each of the X-ray detection elements 1775.

The counting unit 109 may be formed from, for example, one or a plurality of electronic circuits (e.g., processors such as a CPU (Central Processing Unit) and an MPU (Micro Processing Unit) and electronic circuits such as an ASIC (Application Specific Integrated Circuits) and an FPGA (Field Programmable Gate Array).

Figure 4:
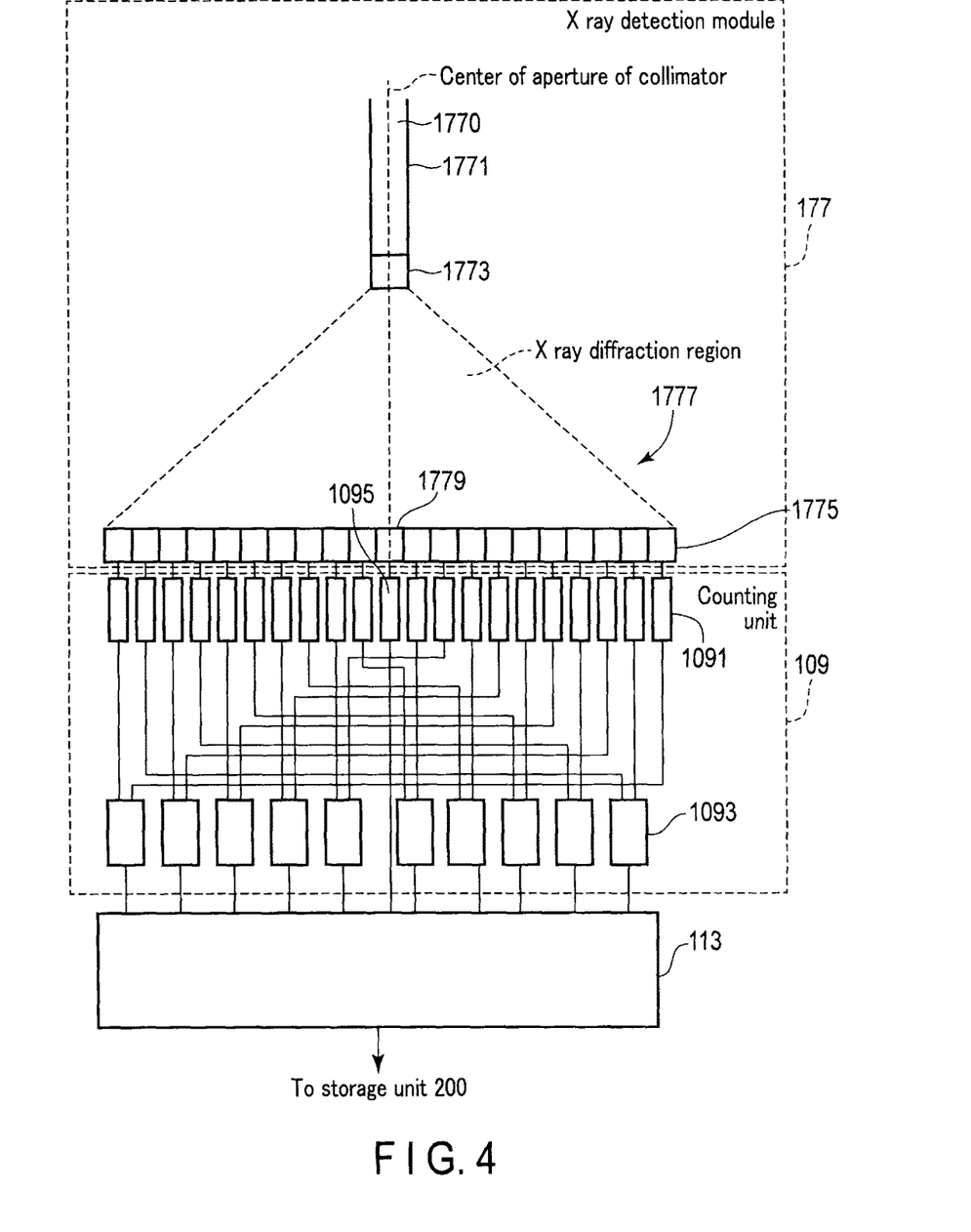
FIG. 4 is a view showing an example of connecting a plurality of counters to a plurality of adders according to this embodiment.

FIG. 4 is a view showing an example of connecting the plurality of counters 1091 to a plurality of adders 1093 in the X-ray detection module 177 and the counting unit 109. As shown in FIG. 4, the plurality of counters 1091 are respectively connected to the plurality of X-ray detection elements 1775. The adders 1093 are connected to the plurality of counters 1091 respectively connected to the plurality of X-ray detection elements 1775 located within the same radius centered on a position (a central element 1779) facing the center of the aperture of the collimator 1771. The counter 1091 connected to the central element 1779 and the plurality of adders 1093 are connected to a noncontact data transmission unit 113. X-ray photons entering the X-ray detection elements increase in energy with a decrease in distance from the central element 1779, and decrease in energy with an increase in distance from the central element 1779. That is, for example, in FIG. 3, the energy of the first monochromatic X-ray is larger than that of the second monochromatic X-ray.

More specifically, the counting unit 109 includes the plurality of counters 1091 which count photons and the plurality of adders 1093 which add a plurality of count numbers output from the plurality of counters 1091. Note that the counting unit 109 may be provided inside or outside the gantry unit 100 independently of the rotating ring 101 via the noncontact data transmission unit 113. The data output from the counting unit 109 is transmitted to the storage unit 200 (to be described later) via the noncontact data transmission unit 113 using magnetic transmission/reception or optical transmission/reception.

The plurality of counters 1091 are respectively connected to the plurality of X-ray detection elements 1775 and count the pulse signals output from the respective X-ray detection elements 1775. The plurality of counters 1091 are connected to the adders 1093 in accordance with the distances (radii) from the center of the X-ray detection element group 1777. Each of the plurality of adders 1093 is connected to some of the plurality of counters 1091 in accordance with the distances from the central position of the X-ray detection element group 1777. Note that no adder 1093 may be connected to the central element 1779. Each adder 1093 adds a plurality of count numbers output from some of the counters 1091. The adder 1093 outputs the sum of count numbers to the storage unit 200 via the noncontact data transmission unit 113.

The storage unit (circuitry) 200 stores the count numbers output via the noncontact data transmission unit 113. More specifically, the storage unit 200 stores a count number for each of a plurality of view angles, each of the plurality of X-ray detection modules 177, and each of a plurality of energy bins. Data concerning a count number (frequency)

for each of a plurality of view angles, each of the plurality of X-ray detection modules 177 (channels), and each of a plurality of energy bins will be referred to as a detection histogram hereinafter. That is, the storage unit 200 stores the count numbers output from the counting unit 109 as a detection histogram. Note that the storage unit 200 may store a detection histogram which has undergone predetermined preprocessing by a preprocessing circuitry (not shown).

Figure 5:
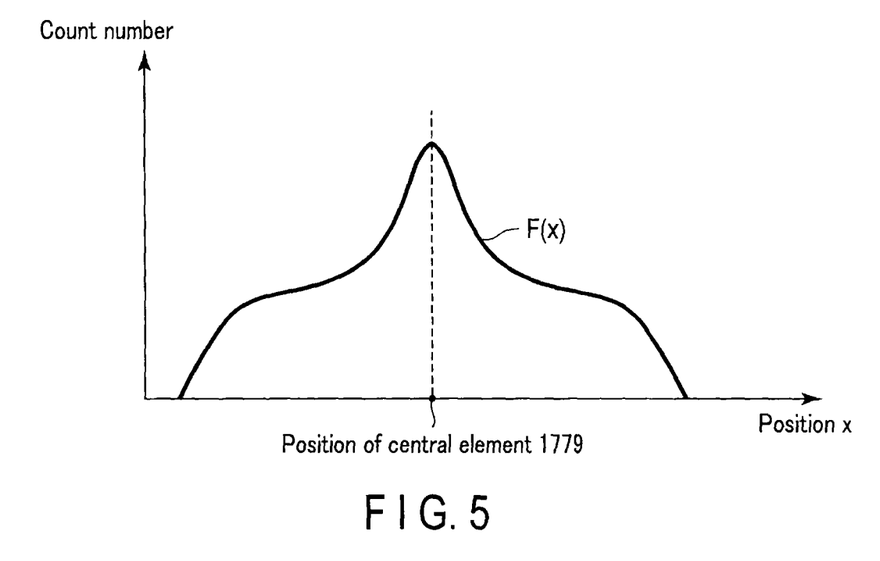
FIG. 5 is a graph showing an example of a histogram concerning the detection of a polychromatic X-ray according to this embodiment.

FIG. 5 shows an example of a detection histogram concerning the detection of a polychromatic X-ray. The ordinate of FIG. 5 represents count numbers. The abscissa of FIG. 5 represents the position of each X-ray detection element. F(x) in FIG. 5 represents a distribution function indicating a count number (detection histogram) corresponding to a position x of each X-ray detection element with reference to the position of the central element 1779. The maximum value (maximum count number) of the distribution function F(x) appears at the position of the central element 1779. This originates from transmitted X-rays transmitted through the diffraction body 1773.

The storage unit 200 stores statistical information corresponding to each of a plurality of energy bins. Statistical information is a probability distribution obtained by normalizing the distribution of a plurality of count values (to be referred to as a count distribution hereinafter) with respect to the positions of the plurality of X-ray detection elements 1775. That is, the storage unit 200 stores a plurality of probability distributions respectively corresponding to a plurality of energy bins. Note that the storage unit 200 may store a plurality of count distributions respectively corresponding to a plurality of energy bins. A plurality of probability distributions respectively correspond to a plurality of energy bins, and hence serve as the bases of the distribution function F(x). Assume that a probability distribution in an energy bin i is represented by a probability distribution function $\Phi_i(x)$. In the probability distribution function $\Phi_i(x)$, i represents a suffix indicating an energy bin number. The suffix i ranges from 1 to n (n is a natural number equal to or more than 2), which are natural numbers representing different energy bins.

The distribution function F(x) and the probability distribution function $\Phi_i(x)$ have an expandable relationship as indicated by $$F(x) = \sum_{i=1}^{n} a_i \Phi_i(x) \quad (1)$$

where $a_i$ corresponds to a weight (total count number) of the expansion coefficient or probability distribution function $\Phi_i(x)$. As indicated by the following expression, the probability distribution function $\Phi_i(x)$ is given as the sum of a transmission probability distribution function $\Phi_{i\ trans}(x)$ originating from the X-rays transmitted through the diffraction body 1773 and a diffraction probability distribution function $\varphi_{i\ diff}(x)$ originating from the X-rays diffracted by the diffraction body 1773. That is, the probability distribution function $\Phi_i(x)$ is defined by the sum of the transmission probability distribution function $\varphi_{i\ trans}(x)$ and the diffraction probability distribution function $\varphi_{i\ diff}(x)$.

$$\Phi_i(x) = \varphi_{i\ trans}(x) \varphi_{i\ diff}(x)$$

As is obvious from, for example, FIG. 6 described later, a plurality of probability distribution functions $\Phi_i(x)$ have no orthogonal relation with different energy bins. That is, the plurality of probability distribution functions $\Phi_i(x)$ serve as the oblique bases of F(x). The non-orthogonal relation can be expressed by equation (2) given below. Note that as indicated by the following equation, a position x is written as a continuous variable for the sake of convenience, but the positions of the plurality of X-ray detection elements 1775 are discrete. For this reason, in a strict sense, integration is summation.

$$\int_x \Phi_i(x) \Phi_j(x) dx = \int_x \langle i | x \rangle \langle x | j \rangle dx = \langle i | j \rangle \neq \delta_{ij} \quad (2)$$

In addition, for the sake of simplicity, assume that each of the plurality of probability distribution functions $\Phi_i(x)$ has been normalized as indicated by $$\int_x \Phi_i(x) dx = 1$$

For the sake of simplicity, assume that the distribution function F(x) and the probability distribution function $\Phi_i(x)$ concerning the energy bin i are expressed by the following expressions:

$$F(x) = \langle x | F \rangle \quad (3)$$

$$\Phi_i(x) = \langle x | i \rangle \quad (4)$$

In this case, the relational expression between the distribution function F(x) and the probability distribution function $\Phi(x)$ is expressed by the following equation by substituting equations (3) and (4) into equation (1).

$$\langle x | F \rangle = \sum_{i=1}^{n} a_i \langle x | i \rangle \quad (5)$$

The following relational expression is obtained by removing the dependence of the position x (removing "bracket x" ($\langle x|$)) from equation (5).

$$|F\rangle = \sum_{i=1}^{n} a_i | i \rangle \quad (6)$$

Equation (6) holds at any position x.

Figure 6:
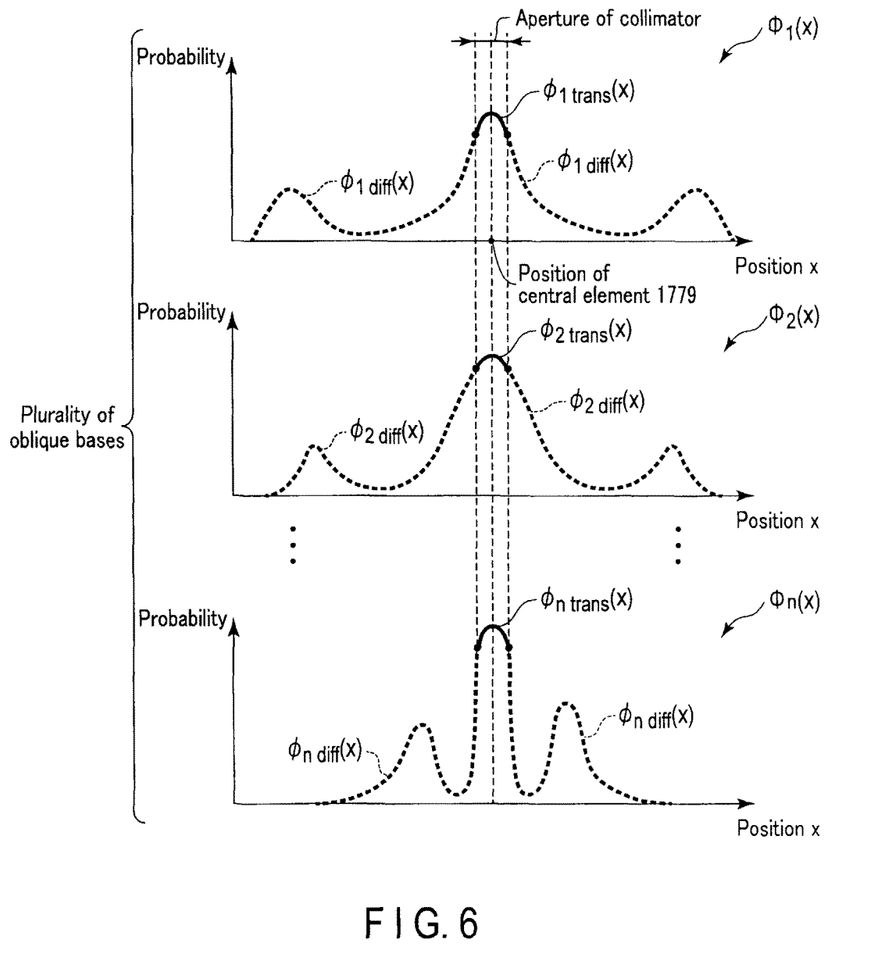
FIG. 6 is a view showing an example of a plurality of oblique bases respectively corresponding to a plurality of energy bins according to this embodiment.

FIG. 6 shows an example of a plurality of oblique bases respectively corresponding to a plurality of energy bins. FIG. 6 shows a plurality of oblique bases respectively corresponding to a plurality of energy bins ($E_1$ to $E_n$), that is, a plurality of probability distribution functions ($\Phi_1(x)$ to $\Phi_n(x)$).

$\Phi_1(x)$ in FIG. 6 is associated with the energy bin $E_1$. FIG. 6 shows how $\Phi_1(x)$ is defined by the sum of $\Phi_{1\ trans}$ indicated by the solid line and $\Phi_{1\ trans}(x)$ indicated by the dotted lines. That is, $\Phi_{1\ trans}(x)$ indicated by the solid line in FIG. 6 corresponds to the probabilities at which monochromatic X-rays belonging to the energy bin $E_1$ are caused to enter the collimator 1771 and a plurality of X-ray detection elements located immediately below the aperture of the collimator 1771 detect photons of the monochromatic X-rays transmitted through the diffraction body 1773. In addition, $\Phi_{1\ diff}(x)$ indicated by the dotted lines in FIG. 6 corresponds to the probabilities at which monochromatic X-rays belonging to the energy bin $E_1$ are caused to enter the collimator 1771 and the X-ray detection elements located at positions except for the position immediately below the aperture of the collimator 1771 detect photons of the monochromatic X-rays diffracted by the diffraction body 1773.

$\Phi_2(x)$ in FIG. 6 is associated with the energy bin $E_2$. FIG. 6 shows how $\Phi_2(x)$ is defined by the sum of $\Phi_{2\ trans}(x)$ indicated by the solid line and $\Phi_{2\ diff}(x)$ indicated by the dotted lines. That is, $\Phi_{2\ trans}(x)$ indicated by the solid line in FIG. 6 corresponds to the probabilities at which monochromatic X-rays belonging to the energy bin $E_2$ are caused to enter the collimator 1771 and a plurality of X-ray detection elements located immediately below the aperture of the collimator 1771 detect photons of the monochromatic X-rays transmitted through the diffraction body 1773. In addition, $\Phi_{2\ diff}(x)$ indicated by the dotted lines in FIG. 6 corresponds to the probabilities at which monochromatic X-rays belonging to the energy bin $E_2$ are caused to enter the collimator 1771 and the X-ray detection elements located at positions except for the position immediately below the aperture of the collimator 1771 detect photons of the monochromatic X-rays diffracted by the diffraction body 1773.

$\Phi_n(x)$ in FIG. 6 is associated with the energy bin $E_n$. FIG. 6 shows how $\Phi_n(x)$ is defined by the sum of $\Phi_{n\ trans}(x)$ indicated by the solid line and $\Phi_{n\ diff}(x)$ indicated by the dotted lines. That is, $\Phi_{n\ trans}(x)$ indicated by the solid line in FIG. 6 corresponds to the probabilities at which monochromatic X-rays belonging to the energy bin $E_n$ are caused to enter the collimator 1771 and a plurality of X-ray detection elements located immediately below the aperture of the collimator 1771 detect photons of the monochromatic X-rays transmitted through the diffraction body 1773. In addition, $\Phi_{n\ diff}(x)$ indicated by the dotted lines in FIG. 6 corresponds to the probabilities at which monochromatic X-rays belonging to the energy bin $E_n$ are caused to enter the collimator 1771 and the X-ray detection elements located at positions except for the position immediately below the aperture of the collimator 1771 detect photons of the monochromatic X-rays diffracted by the diffraction body 1773.

Each of a plurality of probability distribution functions ($\Phi_i(x)$) is defined by, for example, diffraction experiments using monochromatic X-rays having a corresponding energy bin and the diffraction body 1773. Note that each of a plurality of probability distribution functions ($\Phi_i(x)$) may be decided by numerical calculations (e.g., numerical simulations) using monochromatic X-rays having a corresponding energy bin and the diffraction body 1773. The storage unit 200 stores the plurality of probability distribution functions $\Phi_i(x)$ decided by diffraction experiments or numerical calculations.

The storage unit 200 stores the medical images reconstructed by the reconstruction unit 400 (to be described later). The storage unit 200 stores information such as operator's instructions, image processing conditions, imaging conditions, and the like input by the input unit 600 (to be described later). The storage unit 200 stores, for example, control programs for controlling the gantry unit 100 and the like for X-ray computed tomography. The storage unit 200 stores a program concerning energy spectrum generation processing (to be described later). The storage unit 200 may be implemented by, for example, various types of memories, an HDD (Hard Disk Drive), and an SSD (Solid-State drive).

The classification unit (circuitry) 300 classifies the photon counts counted by the counting unit 109 for each energy bin. More specifically, the classification unit 300 generates an energy spectrum indicating a plurality of photon counts respectively corresponding to a plurality of energy bins by using statistical information. That is, the classification unit 300 generates, based on a plurality of probability distributions and a detection histogram, the energy spectrum of the detection histogram corresponding to each of a plurality of energy bins.

More specifically, the classification unit 300 expands the distribution function F(x) corresponding to a detection histogram (to be referred to as spectrum expansion hereinafter) by using the probability distribution function $\Phi_i(x)$. The classification unit 300 decides an expansion coefficient $a_i$ by spectrum expansion. The classification unit 300 generates an energy spectrum concerning the detection histogram based on the decided expansion coefficient $a_i$ and the plurality of probability distribution functions $\Phi_i(x)$.

Spectrum expansion and the derivation of the expansion coefficient $a_i$ by the classification unit 300 will be described below. As indicated by the following equation, the classification unit 300 multiplies the two sides of equation (6) by "bracket j" ($\langle j|$: the Hermitian conjugate of a probability distribution function $\Phi(x)$ concerning an energy bin j) from the left. The following holds when the two sides of equation (6) are multiplied by "bracket j" ($\langle j|$) from the left:

$$\langle j | F \rangle = \sum_{i=1}^{n} a_i \langle j | i \rangle \tag{7}$$

The classification unit 300 calculates "bracket jF" ($\langle j|F\rangle$) of the left-hand side of equation (7) throughout all the energy bins (j=1 to n). More specifically, "bracket jF" ($\langle j|F\rangle$) is calculated by $$\langle j | F \rangle = \int_x \Phi_j(x) F(x) dx \tag{8}$$

For the sake of simplicity, "bracket jF" ($\langle j|F\rangle$) is defined as follows:

$$\langle j | F \rangle \equiv F_j \tag{9}$$

Equation (10) given below is obtained by substituting expression (9) into equation (7).

$$F_j = \sum_{i=1}^{n} a_i \langle j | i \rangle \tag{10}$$

Equation (10) can be written in a matrix format as follows:

$$\begin{pmatrix} F_1 \\ \vdots \\ F_j \\ \vdots \\ F_n \end{pmatrix} = \begin{pmatrix} \langle 1|1\rangle & \cdots & \langle 1|i\rangle & \cdots & \langle 1|n\rangle \\ \vdots & \cdots & \vdots & \cdots & \vdots \\ \langle j|1\rangle & \cdots & \langle j|i\rangle & \cdots & \langle j|n\rangle \\ \vdots & \cdots & \vdots & \cdots & \vdots \\ \langle n|1\rangle & \cdots & \langle n|i\rangle & \cdots & \langle n|n\rangle \end{pmatrix} \begin{pmatrix} a_1 \\ \vdots \\ a_i \\ \vdots \\ a_n \end{pmatrix} \tag{11}$$

For the sake of simplicity, the matrix in equation (11) is defined as N as follows. The matrix N is an n×n matrix including "bracket jF" ($\langle j|F\rangle$) as a component.

$$N \equiv \begin{pmatrix} \langle 1|1\rangle & \cdots & \langle 1|i\rangle & \cdots & \langle 1|n\rangle \\ \vdots & \cdots & \vdots & \cdots & \vdots \\ \langle j|1\rangle & \cdots & \langle j|i\rangle & \cdots & \langle j|n\rangle \\ \vdots & \cdots & \vdots & \cdots & \vdots \\ \langle n|1\rangle & \cdots & \langle n|i\rangle & \cdots & \langle n|n\rangle \end{pmatrix} \quad (12)$$

Expression (12) is rewritten as follows when expression (12) is applied to equation (11).

$$\begin{pmatrix} F_1 \\ \vdots \\ F_j \\ \vdots \\ F_n \end{pmatrix} = N \begin{pmatrix} a_1 \\ \vdots \\ a_i \\ \vdots \\ a_n \end{pmatrix} \quad (13)$$

Since a plurality of probability distribution functions $\Phi_i(x)$ differ from each other, the matrix N in expression (12) has an inverse matrix $N^{-1}$. That is, since a plurality of probability distribution functions $\Phi_i(x)$ respectively corresponding a plurality of energy bins are linearly independent, the matrix N has the inverse matrix $N^{-1}$. The classification unit 300 calculates n×n matrix elements in the matrix N based on a plurality of probability distribution functions $\Phi_i(x)$. If the matrix N is a symmetric matrix, the number of matrix elements calculated by classification unit 300 will be n(n−1)/2. Matrix elements are calculated by equation (2). For example, the classification unit 300 calculates the inverse matrix $N^{-1}$ of N based on the calculated matrix elements. Note that the inverse matrix $N^{-1}$ of the matrix N may be stored in the storage unit 200 in advance.

The following equation is obtained by replacing the two sides of expression (12) upon applying the inverse matrix $N^{-1}$ of the matrix N to the two sides.

$$\begin{pmatrix} a_1 \\ \vdots \\ a_i \\ \vdots \\ a_n \end{pmatrix} = N^{-1} \begin{pmatrix} F_1 \\ \vdots \\ F_j \\ \vdots \\ F_n \end{pmatrix} \quad (14)$$

Equation (14) is rewritten as follows by using equation (8) and expression (9):

$$\begin{pmatrix} a_1 \\ \vdots \\ a_i \\ \vdots \\ a_n \end{pmatrix} = N^{-1} \begin{pmatrix} \langle 1|F\rangle \\ \vdots \\ \langle j|F\rangle \\ \vdots \\ \langle n|F\rangle \end{pmatrix} \quad (15)$$

$$= N^{-1} \begin{pmatrix} \int_x \Phi_1(x)F(x)dx \\ \vdots \\ \int_x \Phi_j(x)F(x)dx \\ \vdots \\ \int_x \Phi_n(x)F(x)dx \end{pmatrix}$$

Figure 7:
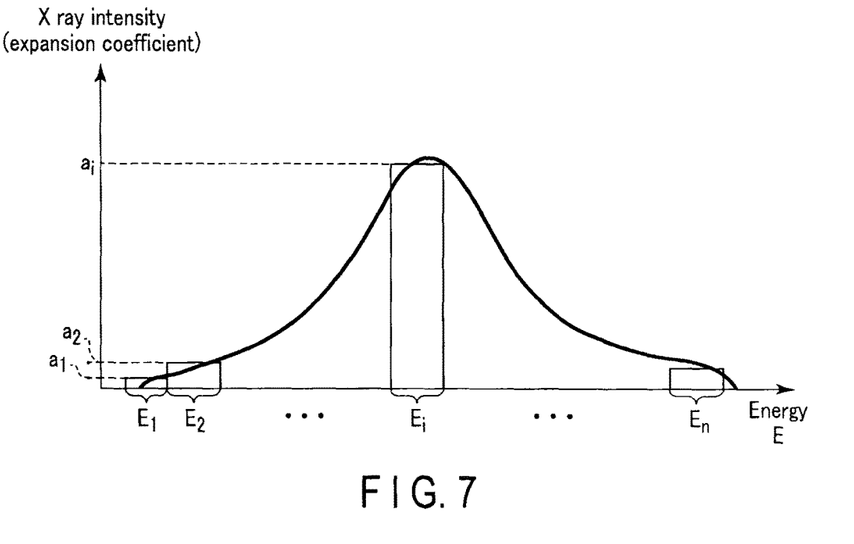
FIG. 7 is a graph showing an example of the energy spectrum of a histogram concerning the detection of a polychromatic X-ray according to this embodiment.

The classification unit 300 decides expansion coefficients $a_i$ by applying the distribution function F(x), the plurality of probability distribution functions $\Phi_i(x)$, and the inverse matrix N of the matrix N to equation (15). The classification unit 300 generates an energy spectrum indicating a plurality of photon counts respectively corresponding to a plurality of energy bins based on the plurality of expansion coefficients $a_i$. FIG. 7 shows an example of the energy spectrum of a detection histogram concerning the detection of a polychromatic X-ray. The ordinate of FIG. 7 corresponds to X-ray intensities, i.e., the expansion coefficients $a_i$.

The classification unit 300 generates an energy spectrum for every two or more view angles and two or more X-ray detection modules (channels) 177. The classification unit 300 outputs the generated energy spectra to the reconstruction unit 400 (to be described later) in correspondence with view angles and channel numbers.

The classification unit 300 may be formed from, for example, one or a plurality of electronic circuits (e.g., processors such as a CPU (Central Processing Unit) and an MPU (Micro Processing Unit) and electronic circuits such as an ASIC (Application Specific Integrated Circuits) and an FPGA (Field Programmable Gate Array).

Figure 8:
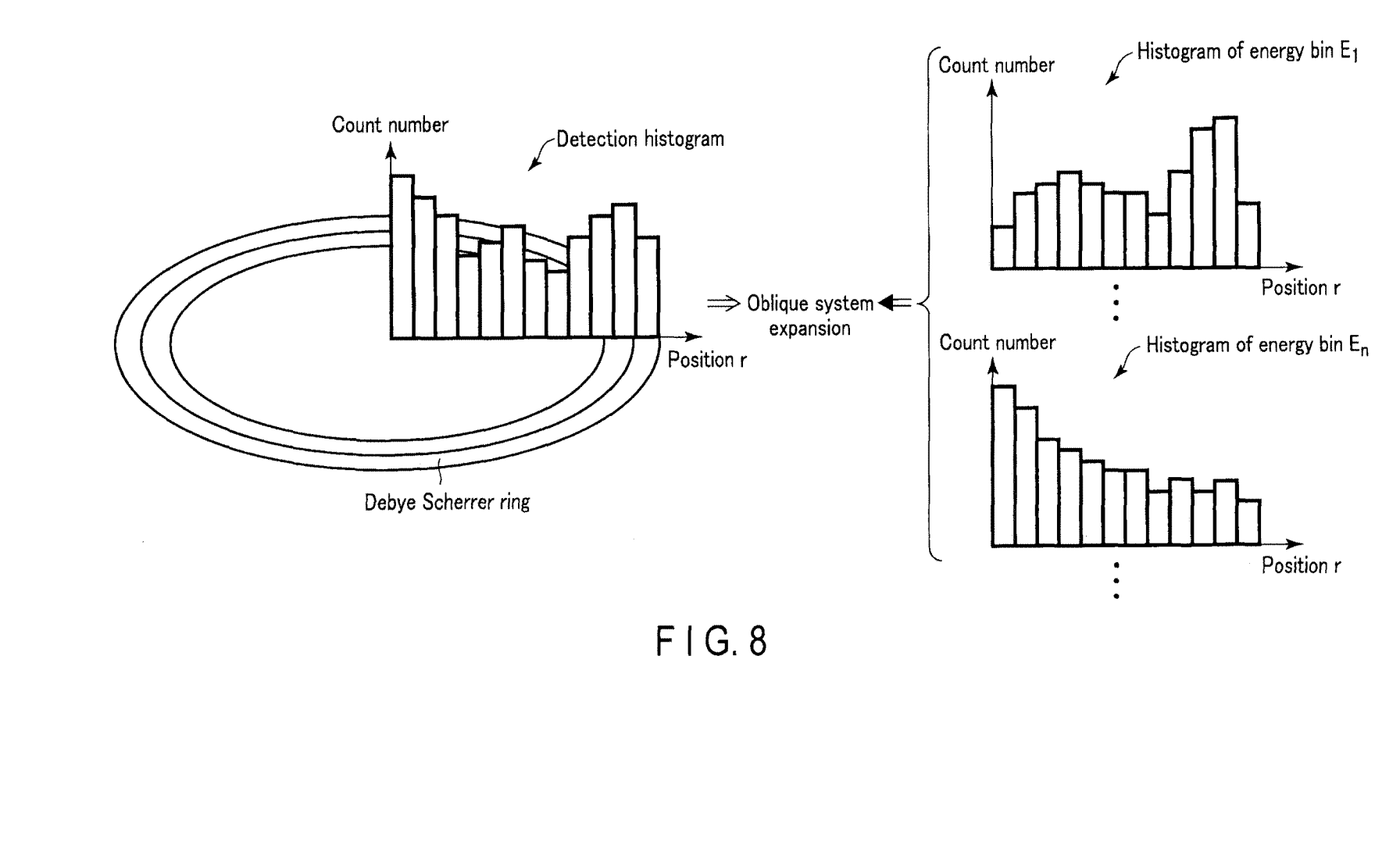
FIG. 8 is a view showing a histogram concerning the detection of a polychromatic X-ray, together with a plurality of histograms respectively corresponding to a plurality of energy bins and serving as the bases of oblique coordinate system according to this embodiment.

FIG. 8 shows a detection histogram concerning the detection of a polychromatic X-ray, together with a plurality of histograms serving as oblique coordinate system bases, which respectively correspond to a plurality of energy bins. Note that spectrum expansion may be performed using a plurality of histograms corresponding to different energy bins shown in FIG. 8. The abscissa of FIG. 8 represents a position r in a radial direction centered on the central element 1779. The ordinate of FIG. 8 represents the count numbers obtained by addition by the adders.

The reconstruction unit 400 reconstructs medical images corresponding to energy bins based on the energy spectra respectively corresponding to a plurality of view angles and the plurality of X-ray detection modules 177. For example, the reconstruction unit 400 reconstructs a medical image by a filtered backprojection method (for example, a convolution backprojection method) or a successive approximation method (for example, the OS-EM method). Note that the reconstruction unit 400 can also reconstruct a plurality of medical images respectively corresponding to a plurality of energy bins based on energy spectra respectively corresponding to a plurality of view angles and the plurality of X-ray detection modules 177.

Note that the reconstruction unit 400 can also generate an energy difference image based on a plurality of medical images respectively corresponding to a plurality of energy bins. In addition, the reconstruction unit 400 can also reconstruct a medical image corresponding to an energy difference based on the energy spectra respectively corresponding to a plurality of view angles and the plurality of X-ray detection modules 177.

The reconstruction unit 400 may be formed from, for example, one or a plurality of electronic circuits (e.g., processors such as a CPU (Central Processing Unit) and an MPU (Micro Processing Unit) and electronic circuits such as an ASIC (Application Specific Integrated Circuits) and an FPGA (Field Programmable Gate Array).

The display unit 500 displays a medical image for each energy bin which is reconstructed by the reconstruction unit 400, conditions set for X-ray computed tomography, and the like.

The input unit (circuitry) 600 inputs the imaging conditions for X-ray computed tomography desired by the operator, the information on an object, and the like. More specifically, the input unit 600 takes various instructions, commands, information, selections, and settings from the operator into this photon counting X-ray CT apparatus 1. Although not shown, the input unit 600 is implemented by a trackball, switch buttons, a mouse, a keyboard, and the like for setting a region of interest and the like. The input unit 600 detects the coordinates of the cursor displayed on a display screen, and outputs the detected coordinates to the control unit 700. Note that the input unit 600 may be a touch panel provided to cover the display screen. In this case, the input unit 600 detects touched and designated coordinates by a coordinate reading principle such as an electromagnetic induction scheme, magnetostriction scheme, or a pressure-sensitive scheme, and outputs the detected coordinates to the control unit 700.

The control unit (circuitry) 700 functions as the main unit of the photon counting X-ray CT apparatus 1. The control unit 700 includes various types of processors such as a CPU (Central Processing Unit) and a memory. The control unit 700 controls a bed (not shown), the gantry unit 100, the rotation driving unit 103, the X-ray generating unit 105 so as to perform X-ray computed tomography based on the examination schedule data and control programs stored in the memory (not shown). More specifically, the control unit 700 temporarily stores, in the memory, information such as operator's instructions and image processing conditions sent from the input unit 600. The control unit 700 controls the bed, the gantry unit 100, the rotation driving unit 103, the X-ray generating unit 105 and the like based on these pieces of information temporarily stored in the memory.

The control unit 700 reads out control programs for the execution of predetermined image generation/display processing, energy spectrum generation processing (to be described later), and the like from the storage unit 200, loads the programs in its own memory, and executes computation/processing concerning various types of processing, and the like.

The control unit 700 may be formed from, for example, one or a plurality of electronic circuits (e.g., processors such as a CPU (Central Processing Unit) and an MPU (Micro Processing Unit) and electronic circuits such as an ASIC (Application Specific Integrated Circuits) and an FPGA (Field Programmable Gate Array).

(Energy Spectrum Generating Function)

An energy spectrum generating function is a function of generating an energy spectrum concerning a detection histogram based on the distribution function F(x) indicating a detection histogram and the plurality of probability distribution functions $\Phi_i(x)$ serving as the oblique bases of F(x). Processing (to be referred to as energy spectrum generation processing hereinafter) concerning the energy spectrum generating function will be described below.

Figure 9:
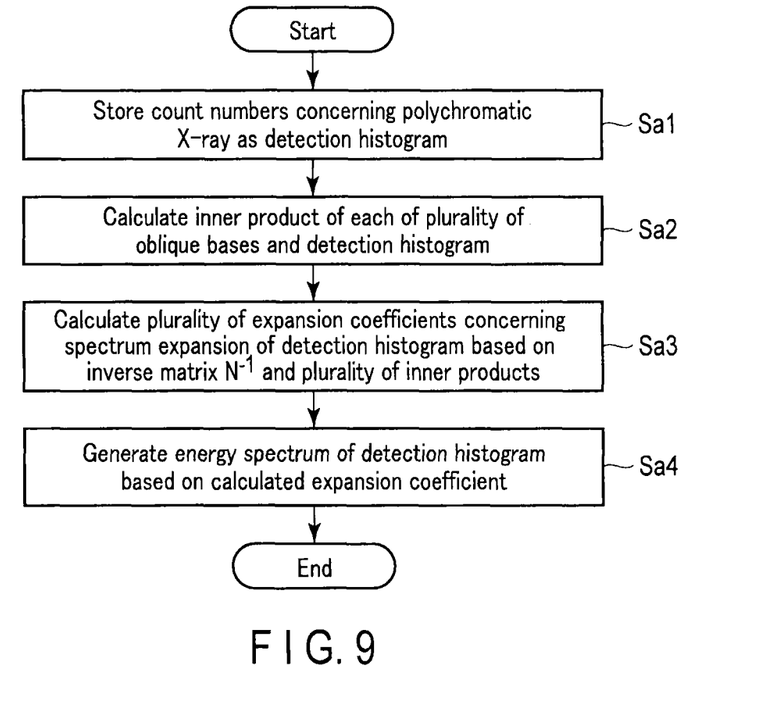
FIG. 9 is a flowchart showing an example of a procedure for the processing of generating an energy spectrum by oblique expansion of a detection histogram using a plurality of oblique bases according to this embodiment.

FIG. 9 is a flowchart showing an example of a procedure for energy spectrum generation processing.

The inverse matrix N of the matrix N is calculated in advance based on a plurality of probability distribution functions ($\Phi_i(x)$) with a plurality of oblique bases. More specifically, n×n matrix elements in the matrix N are calculated by using equation (2). The inverse matrix $N^{-1}$ of the matrix N is calculated based on the n×n matrix elements. The calculated inverse matrix $N^{-1}$ is stored in the storage unit 200 in advance. Count numbers concerning a polychromatic X-ray are stored as a detection histogram (step Sa1). The inner product of each of a plurality of oblique bases (a plurality of probability distribution functions $\Phi_i(x)$) respectively corresponding to a plurality of energy bins and a detection histogram (distribution function F(x)) is calculated (step Sa2). In this case, the inner product is "bracket jF" (<j|F>) corresponding to equation (7). Inner products are calculated for a plurality of energy bins (j=1 to n).

A plurality of expansion coefficients a are calculated based on a plurality of inner products (<j|F>) respectively corresponding to a plurality of energy bins (j=1 to n) and the inverse matrix N (step Sa3). More specifically, a plurality of expansion coefficients $a_i$ are calculated by substituting a plurality of inner products (<j|F>) and the inverse matrix N into equation (15).

The energy spectrum of the detection histogram is decided by the plurality of calculated expansion coefficients $a_i$ (step Sa4). The reconstruction unit 400 reconstructs a medical image corresponding to each of a plurality of energy bins based on the decided energy spectrum.

According to the above arrangement, the following effects can be obtained.

The photon counting X-ray CT apparatus 1 can generate the energy spectrum of a detection histogram from the detection histogram by using statistical information. This makes it possible to generate an energy spectrum concerning a polychromatic X-ray entering the collimator 1771. In addition, the photon counting X-ray CT apparatus 1 can reconstruct a medical image corresponding to each of a plurality of energy bins based on the generated energy spectrum. That is, the photon counting X-ray CT apparatus 1 can perform spectrum imaging.

Note that as a modification of this embodiment, when implementing the technical idea of the photon counting X-ray CT apparatus 1 in the form of a medical image processing apparatus, the apparatus includes, for example, the constituent elements enclosed by a dotted line 2 in the block diagram of FIG. 1. Each processing in the energy spectrum generating function is the same as that in this embodiment.

In addition, each function according to this embodiment can be implemented by installing a program for executing energy spectrum generation processing in a computer such as a workstation and loading it in the memory. In this case, the program which can cause the computer to execute this method can be distributed by being stored in storage media such as magnetic disks (floppy disks, hard disks, and the like), optical disks (CD-ROMs, DVDs, and the like), and semiconductor memories.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. An X-ray computed tomography apparatus, comprising:
    an X-ray tube configured to generate X-rays;
    a plurality of collimators including a plurality of through holes, respectively, which collimate an X-ray generated by the X-ray tube, and a plurality of diffraction bodies provided in the through holes respectively, diffracting the X-ray at an angle corresponding to an energy of the X-ray;

a plurality of X-ray detection elements provided at predetermined distances from each of the diffraction bodies;

counting circuitry configured to count a number of photons originating from the X-ray based on outputs from the X-ray detection elements;

a memory storing statistical information including a spatial count distribution of a plurality of count values with respect to spatial positions of the X-ray detection elements;

classification circuitry configured to determine respective numbers of counted photons for each of a plurality of energy bins by using the stored statistical information including the spatial count distribution; and reconstruction circuitry configured to reconstruct a respective medical image for each energy bin of the energy bins, based on the number of photons determined for each of the energy bins.

2. The X-ray computed tomography apparatus of claim 1, wherein the classification circuitry is further configured to generate an energy spectrum by determining the numbers of counted photons for each of the energy bins by using the statistical information, and the reconstruction circuitry is further configured to reconstruct the respective medical image for each energy bin of the energy bins, based on the generated energy spectrum.

3. The X-ray computed tomography apparatus of claim 1, wherein the statistical information is a probability distribution obtained by normalizing the spatial count distribution.

4. The X-ray computed tomography apparatus of claim 1, wherein the statistical information is the spatial count distribution.

5. The X-ray computed tomography apparatus of claim 1, wherein the statistical information includes a plurality of bases of an oblique coordinate system configured to expand the spatial count distribution of the numbers of counted photons corresponding to the spatial positions of the plurality of X-ray detection elements for each of the energy bins, and the classification circuitry is further configured to determine the numbers of counted photons for each of the energy bins by using the bases of the oblique coordinate system.

6. The X-ray computed tomography apparatus of claim 1, wherein the diffraction body is a metal or a crystal powder.

7. The X-ray computed tomography apparatus of claim 1, wherein the diffraction body is provided on a rear surface side of the through hole.

8. The X-ray computed tomography apparatus of claim 1, wherein each of the diffraction bodies is provided on a path of the X-ray passing through each of the through holes.

9. A medical image processing apparatus, comprising:

a memory storing a number of photons originating from an X-ray and statistical information including a spatial count distribution of a plurality of count values with respect to spatial positions of the plurality of X-ray detection elements;

classification circuitry configured to determine respective numbers of photons for each of a plurality of energy bins by using the stored statistical information, including the spatial count distribution; and reconstruction circuitry configured to reconstruct a respective medical image for each energy bin of the energy bins, based on the number of photons determined for each of the energy bins.

10. The medical image processing apparatus of claim 9, wherein the classification circuitry is further configured to generate an energy spectrum by determining the numbers of counted photons for each of the energy bins by using the statistical information, and the reconstruction circuitry is further configured to reconstruct the respective medical image for each energy bin of the energy bins, based on the generated energy spectrum.

11. The medical image processing apparatus of claim 9, wherein the statistical information is a probability distribution obtained by normalizing the spatial count distribution.

12. The medical image processing apparatus of claim 9, wherein the statistical information is the spatial count distribution.

13. The medical image processing apparatus of claim 9, wherein the statistical information includes a plurality of bases of an oblique coordinate system configured to expand the spatial count distribution of the numbers of photons corresponding to the spatial positions of the plurality of X-ray detection elements for each of the energy bins, and the classification circuitry is further configured to determine the numbers of photons for each of the energy bins by using the bases of the oblique coordinate system.

14. A medical image processing method, comprising:

storing the number of photons originating from an X-ray and statistical information including a spatial count distribution of a plurality of count values with respect to spatial positions of the plurality of X-ray detection elements; and determining respective numbers of photons for each of a plurality of energy bins by using the stored statistical information, including the spatial count distribution; and reconstructing a respective medical image for each energy bin of the energy bins, based on the number of photons determined for each of the energy bins.

15. The medical image processing method of claim 14, wherein the determining further includes generating an energy spectrum by determining the numbers of photons for each of the energy bins by using the statistical information, and the reconstructing step further includes reconstructing the respective medical image for each energy bin of the energy bins, based on the generated energy spectrum.

16. The medical image processing method of claim 14, wherein the statistical information is a probability distribution obtained by normalizing the spatial count distribution.

17. The medical image processing method of claim 14, wherein the statistical information is the spatial count distribution.

18. The medical image processing method of claim 14, wherein the statistical information includes a plurality of bases of an oblique coordinate system configured to expand the spatial count distribution of the numbers of photons corresponding to the spatial positions of the plurality of X-ray detection elements for each of the energy bins, and the determining includes determining the numbers of photons for each of the energy bins by using the bases of the oblique coordinate system.

* * * * *